(12) United States Patent
Kim

(10) Patent No.: US 9,072,690 B2
(45) Date of Patent: Jul. 7, 2015

(54) TUMOR ANTIGEN PROTEINS OR GENES OF POLO-LIKE KINASE 1

(75) Inventor: Tai Gyu Kim, Seoul (KR)

(73) Assignee: THE CATHOLIC UNIVERSITY OF KOREA INDUSTRY-ACADEMIC COOPERATION FOUNDATION (KR)

( * ) Notice: Subject to any disclaimer, the term of this patent is extended or adjusted under 35 U.S.C. 154(b) by 0 days.

(21) Appl. No.: 14/113,046

(22) PCT Filed: Feb. 8, 2012

(86) PCT No.: PCT/KR2012/000928
§ 371 (c)(1),
(2), (4) Date: Dec. 30, 2013

(87) PCT Pub. No.: WO2012/144726
PCT Pub. Date: Oct. 26, 2012

(65) Prior Publication Data
US 2014/0105923 A1    Apr. 17, 2014

(30) Foreign Application Priority Data

Apr. 21, 2011 (KR) .................. 10-2011-0037522

(51) Int. Cl.
*A61K 35/00* (2006.01)
*A61K 39/00* (2006.01)
*A61K 38/45* (2006.01)
*C12N 9/12* (2006.01)
*C07K 14/47* (2006.01)

(52) U.S. Cl.
CPC .............. *A61K 39/0011* (2013.01); *A61K 38/45* (2013.01); *C12N 9/12* (2013.01); *C12Y 207/11021* (2013.01); *A61K 39/00* (2013.01); *C07K 14/4748* (2013.01); *A61K 35/00* (2013.01); *A61K 2039/5154* (2013.01); *A61K 2039/53* (2013.01)

(58) Field of Classification Search
None
See application file for complete search history.

(56) References Cited

U.S. PATENT DOCUMENTS 6,358,738 B1 * 3/2002 Erikson et al. ................ 435/375

OTHER PUBLICATIONS

Skolnick et al. (Trends in Biotech., 18(1):34-39, 2000).*
Ezzell (J. NIH Res. 1995 7:46).*
Spitler (Cancer Biotherapy, 1995, 10:1-3).*
Boon (Adv. Can. Res. 1992 58:177-210).*
Burgess et al, Journal of Cell Biology vol. 111 Nov. 1990 2129-2138.*
Lazar et al Molecular and Cellular Biology Mar. 1988 vol. 8 No. 3 1247-1252.*
Jung-Sun Park, et al., Topoisomerase II alpha as a universal tumor antigen: antitumor immunity in murine tumor models and H-2Kb-restricted T cell epitope, Cancer Immunol Immunother, 2010, pp. 747-757.
Birgit Spankuch-Schmitt, et al., Downregulation of human polo-like kinase activity by antisense oligonucleotides induces growth inhibition in cancer cells, Oncogene, 2002, pp. 3162-3171.
Diez-Roux, G., et al. Mus musculus polo-like kinase 1 (Plk1), mRNA, NCBI GenBank, 2011.
International Search Report—PCT/KR2012/000928 dated Sep. 26, 2012.

* cited by examiner

*Primary Examiner* — Sheela J Huff
(74) *Attorney, Agent, or Firm* — Cantor Colburn LLP

(57) ABSTRACT

The present invention relates to tumor antigen proteins or genes derived from polo-like kinase 1. As a result of the formation of a complex by binding polo-like kinase 1-derived proteins or variants having characteristics functionally identical to the proteins with MHC class I antigens or II antigens, the complex can be recognized by cytotoxic T lymphocytes. Therefore, the polo-like kinase 1-derived proteins or variants are identified as a tumor antigen which can be generally used in tumor immunotherapy.

7 Claims, 10 Drawing Sheets

US 9,072,690 B2

TUMOR ANTIGEN PROTEINS OR GENES OF POLO-LIKE KINASE 1

TECHNICAL FIELD

The present invention relates to a tumor antigen protein or gene of polo-like kinase 1, more particularly to a tumor antigen comprising a polo-like kinase 1-derived protein consisting of amino acid sequence of SEQ ID NO: 1 or SEQ ID NO: 3 or a variant having characteristics functionally identical to the protein, which can be recognized by cytotoxic T lymphocytes after binding with MHC class I antigen or II antigen.

BACKGROUND ART

Cell division is dependent on mitosis, and relates to cancer development and progression.

Polo-like kinase 1 (Plk1), a serine-threonine kinase, has a key role in the regulation of cell division, including mitotic entry, spindle formation, chromosome segregation, and cytokinesis[1-3].

Moreover, downregulation of Plk1 by antisense oligonucleotides and siRNA (small interfering RNA) results in a marked reduction in proliferation and increase in apoptosis in tumor cells, but not in normal cells in vitro, and has been demonstrated to be a powerful suppression of tumor growth in a xenogenic model.

Recently, Several Plk1 inhibitors, including scytonemin, B-2536, HMN-214, ON-01910, and poloxin, are under development as potential treatments for cancer, with some of them in clinical trials.

Many tumor antigens are tolerogenic as self-antigens, it is often difficult to induce a specific immune responses against them. Dendritic cells (DC), as the most potent antigen-presenting cells, can break tolerance against self-antigens by effectively priming naive T cells in vitro and in vivo.

Meanwhile, the molecules that regulate the cell cycle, Aurora A, Topoisomerase II α (Top IIα), Foxm1, and Ran have been reported to be tumor antigens. Aurora A was defined as a novel target of cellular immunotherapy for leukemia.

The immunogenicity of TopIIa was demonstrated in a mouse system by vaccination with mRNA electroporated DCs.

Foxm1 and Ran peptide can induce cytotoxic T lymphocytes (CTL) activity in human PBMC and in human leukocyte antigen (HLA)-A2 transgenic mice.

Plk1 is tightly associated with these proteins as a key cell cycle protein. If P1K1 induced tumor cell-specific immune response, it would be used as a target of immunotherapy for specific removal of tumor cell. However, this tumor cell-specific immune response of P1k1 is not known by now.

DISCLOSURE

Technical Problem

It is an object of the present invention to provide a tumor antigen comprising a polo-like kinase 1-derived protein consisting of amino acid sequence of SEQ ID NO: 1 or SEQ ID NO: 3 or a variant having characteristics functionally identical to the protein, which can be recognized by cytotoxic T lymphocytes after binding with MHC class I antigen or II antigen.

However, other objects and advantage of the present invention will become apparent from the detailed description to follow taken in conjugation with the appended claims and drawings.

Technical Solution

The present invention provides a tumor antigen comprising a polo-like kinase 1-derived protein consisting of amino acid sequence of SEQ ID NO: 1 or SEQ ID NO: 3 or a variant having characteristics functionally identical to the protein, which can be recognized by cytotoxic T lymphocytes after binding with MHC class I antigen or II antigen.

In one embodiment of the present invention, there is provided a composition for preventing or treating tumor comprising the tumor antigen as an active ingredient.

In another embodiment of the present invention, there is provided a method for preventing or treating tumor comprising administering the tumor antigen.

In another embodiment of the present invention, there is provided an antigen-presenting cell which has a complex of MHC class I antigen or II antigen and the tumor antigen presented on the surface of cell having antigen-presentation capacity.

In another embodiment of the present invention, there is provided a method for preparing an antigen-presenting cell having a complex of MHC class I antigen or II antigen and the tumor antigen presented on its surface, which comprises introducing a gene coding for the tumor antigen into cells having antigen-presentation capacity.

In another embodiment of the present invention, there is provided a composition for preventing or treating tumor comprising the antigen-presenting cells.

In another embodiment of the present invention, there is provided a method for preventing or treating tumor comprising administering the antigen-presenting cells.

In another embodiment of the present invention, there is provided a cytotoxic T lymphocyte which specifically recognizes a complex of MHC class I antigen or II antigen and the tumor antigen presented on the surface of the antigen-presenting cells.

In another embodiment of the present invention, there is provided a composition for preventing or treating tumor comprising the cytotoxic T lymphocytes.

In another embodiment of the present invention, there is provided a method for preventing or treating tumor comprising administering the Cytotoxic T lymphocytes.

Conventionally, it is not known that that Polo-like kinase 1 can be used as a target of immunotherapy for tumor cell-specific removal by inducing tumor cell-specific immune response. In this regard, the present inventors confirmed that P1k1 can be a new target of T lymphocytes as a tumor antigen for a wide use immunotherapy, and have completed the present invention.

Hereinafter, the present invention will be described in detail.

Particularly, the present invention provide a tumor antigen comprising a polo-like kinase 1-derived protein consisting of amino acid sequence of SEQ ID NO: 1 or SEQ ID NO: 3 or a variant having characteristics functionally identical to the protein, which can be recognized by cytotoxic T lymphocytes after binding with MHC class I antigen or II antigen.

In the tumor antigen of the present invention, the polo-like kinase 1 is preferably derived from mouse or human, but it is not limited to them.

As used herein the term "variant having characteristics functionally identical to the protein" means that it has functionally equivalent characteristics with the tumor antigen protein derived from polo-like kinase 1 even if parts of amino acid of the tumor antigen are substituted or deleted.

In the tumor antigen of the present invention, the tumor antigen protein consisting of amino acid sequence of SEQ ID NO: 1 can be encoded by a gene consisting of base sequence of SEQ ID NO: 2, and the tumor antigen protein consisting of amino acid sequence of SEQ ID NO: 3 can be encoded by a gene consisting of base sequence of SEQ ID NO: 4.

In addition, the present invention provides a tumor antigen gene consisting of base sequence of SEQ ID NO: 2 or SEQ ID NO: 4, which codes for the tumor antigen protein of the present invention, wherein the gene can be DNA or RNA form.

In addition, the present invention provides a composition for preventing or treating tumor comprising the tumor antigen of the present invention as an active ingredient.

In the composition of the present invention, the tumor may be expressing a Polo-like kinase 1, and the tumor expressing a Polo-like kinase may be selected from the group consisting of malignant melanoma, lymphoma, colorectal cancer, glioma, renal cancer, ovarian cancer, breast cancer, glioblastoma, leukemia and cervical cancer, but it is not limited to them.

In addition, the present invention provides a method for preventing or treating tumor, which comprises administering an effective dose of the tumor antigen of the present invention to an individual in need thereof.

A medicine, which contains the tumor antigen protein of the present invention or a variant having characteristics functionally identical to the protein as an active ingredient, can prevent tumor, suppress its relapse, or treat tumor for example by administering the tumor antigen of the present invention singly or combined with cell carrier to tumor patients. Tumor antigen of the present invention can bind with MHC class I antigen or II antigen in antigen presentation cell and be presented on the surface of the cell in high density. Accordingly, tumor-specific CTLs can efficiently proliferate in the body, hereby tumor prevention, relapse suppression, or therapy can be achieved.

The tumor antigen of present invention may be used as a single or mixture of two or more tumor antigen proteins or variants having characteristics functionally identical to the proteins. To achieve effective cell-mediated immunity, the tumor antigen of the present invention may be administered with immunopotentiators by injection or orally in granular formulation. For preventing or treating tumor, the effective dose of the present tumor antigen can be properly selected depending on the patient's age, gender, severity of the illness, preferably the tumor antigen may be administered in 0.1 to 500 mg per day.

In addition, the present invention provides an antigen-presenting cell which has a complex of MHC class I antigen or II antigen and the tumor antigen of the present invention presented on the surface of cell having antigen-presentation capacity.

In the antigen-presenting cell of the present invention, the cell having antigen-presentation capacity may be selected from the group consisting of dendritic cell, mononuclear cell, CD4 T cell, B cell and gamma delta T cell, preferably CD4 T cell, B cell and gamma delta T cell may be naive state, activated state or expanded state but it is not limited to them.

In addition, the present invention provides a method for preparing an antigen-presenting cell having a complex of MHC class I antigen or II antigen and the tumor antigen of the present invention presented on its surface, which comprises introducing a gene coding for the tumor antigen of the present invention into cells having antigen-presentation capacity.

The above gene may be DNA or RNA form.

The method for introducing DNA of the present invention into cells includes, but not limited to, virus vector method. The virus vector method may introduce DNA of the present invention, for example mixed with DNA virus or RNA virus selected from the group consisting of retrovirus, lentivirus, adenovirus, adeno-associated virus, herpesvirus, waxinia virus, pox virus, polio virus, sindbis virus, etc. In addition, the method for introducing RNA of the present invention into cells includes, but limited to, electropolation method.

In addition, the present invention provides a composition for preventing or treating tumor comprising the antigen-presenting cell of the present invention.

In addition, the present invention provides a method for preventing or treating tumor, which comprises administering an effective dose of the antigen-presenting cell of the present invention to an individual in need thereof.

The antigen-presenting cells of present invention may be formulated in the form of cell theraphy products. To achieve effective cell-mediated immunity, the antigen-presenting cells of the present invention may be administered with immunopotentiators by injection or orally in granular formulation. For preventing or treating tumor, the effective dose of the present antigen-presenting cells can be properly selected depending on the patient's age, gender, severity of the illness, preferably the antigen-presenting cells may be administered in 0.1 to 500 mg per day.

In addition, the present invention provides a cytotoxic T lymphocyte which specifically recognizes a complex of MHC class I antigen or II antigen and the tumor antigen of the present invention presented on the surface of the antigen-presenting cell of the present invention.

In the cytotoxic T lymphocyte of the present invention, the cytotoxic T lymphocyte preferably comprises, but not limited to, CD4 T cell or CD8 T cell.

In addition, the present invention provides a composition for preventing or treating tumor comprising the cytotoxic T lymphocyte of the present invention.

In addition, the present invention provides a method for preventing or treating tumor, which comprises administering an effective dose of the cytotoxic T lymphocyte of the present invention to an individual in need thereof.

The cytotoxic T lymphocytes of present invention may be formulated in the form of cell theraphy products. To achieve effective cell-mediated immunity, the cytotoxic T lymphocytes of the present invention may be administered with immunopotentiators by injection or orally in granular formulation. For preventing or treating tumor, the effective dose of the present cytotoxic T lymphocytes can be properly selected depending on the patient's age, gender, severity of the illness, preferably the cytotoxic T lymphocytes may be administered in 0.1 to 500 mg per day.

Advantageous Effects

The present polo-like kinase 1-derived proteins or variants having characteristics functionally identical to the proteins can bind with MHC class I antigens or II antigens to form a complex which can be recognized by cytotoxic T lymphocytes. Therefore, the polo-like kinase 1-derived protein or its variant is identified as a tumor antigen which can be widely used in tumor immunotherapy.

MODE FOR INVENTION

Figure 1:
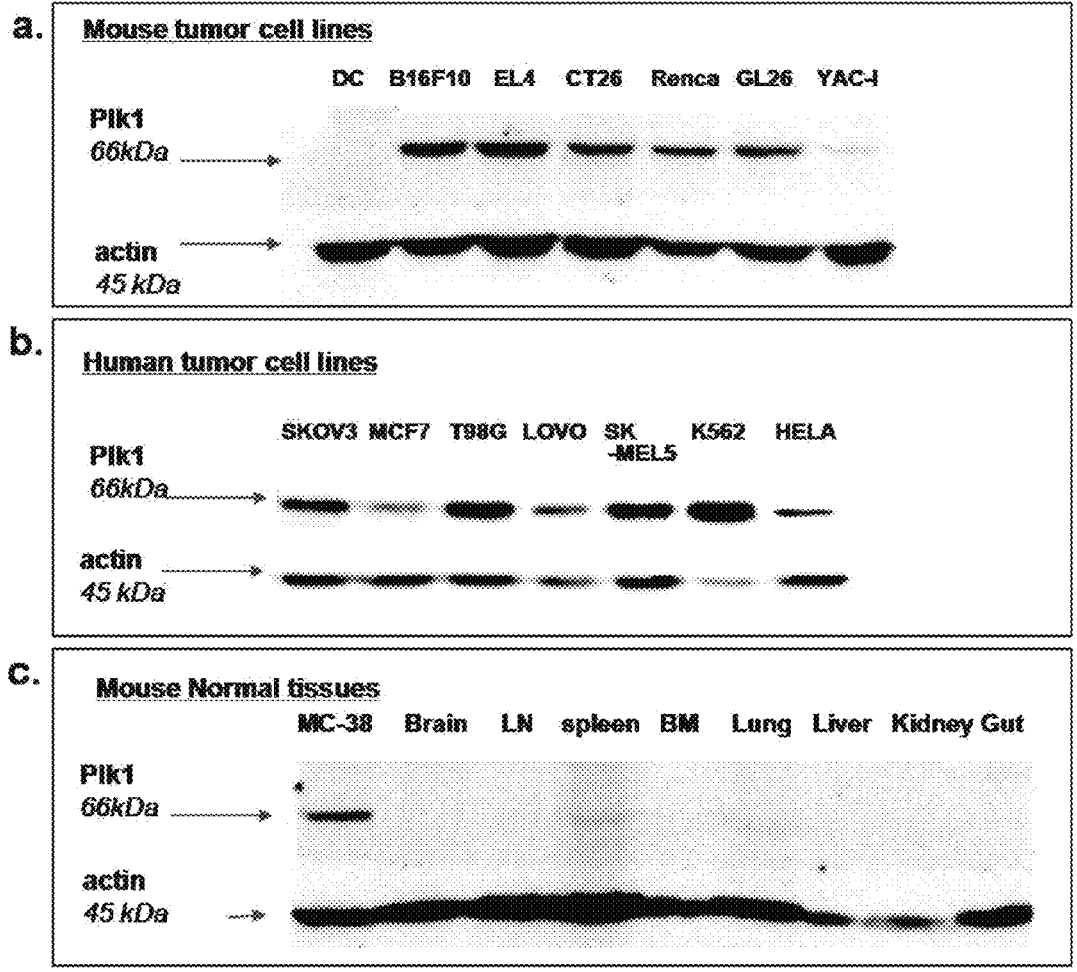
FIG. 1 shows the expression of Plk1 in mouse tumor cell lines, human tumor cell lines, and normal mouse tissues confirmed by western boltting.

Hereinafter, the present invention will be described in more detail with reference to the following Examples. These examples are provided only for illustrating the present invention and should not be construed as limiting the scope and spirit of the present invention.

EXAMPLES

For better understanding of the present invention, as laboratory animals used in examples, female C57BL/6 mice (H-2b, 6-8 weeks old) and BALB/c mice (H-2d, 6-8 weeks old) were purchased from Orient Bio (Kapung, Korea). The mice were maintained and treated according to the laboratory animals guideline of the Animal Protection Local Society.

Human peripheral blood were obtained from seven healthy volunteers, peripheral mononuclear cells were separated by Ficoll-Hypaque (Amersham Pharmacia Biotech, USA) density gradient centrifugation. Human leukocyte HLA-A subtypes of volunteers were decided by typing of sequence base in HLA laboratory. Consent and written acknowledgment for this study were obtained from IRB research committee of Catholic University Medical School.

Tumor cell lines, GL26 (H-2b; glioma), MC-38 (H-2b; colorectal cancer), B16F10 (H-2b; malignant melanoma), Renaca (H-2d; renal cancer) and CT26 (H-2d; colorectal cancer) were cultured in complete DMEM (Dulbecco's Moified Eagle Medium) supplemented with 10% FBS (fetal bovine serum, Gibco, Grand Island, N.Y., USA), 2 mM glutamine, 100 U/mL penicillin and 100 μg/mL streptomycin. EL4 (H-2b; lymphoma) and YAC-1 (H-2a; lymphoma) were cultured in complete RPMI-1640 (Cambrex) medium supplemented with 10% FBS (fetal bovine serum, Gibco, Grand Island, N.Y., USA), 2 mM glutamine, 100 U/mL penicillin and 100 μg/mL streptomycin. GL26 was kindly provided by Dr. John S Yu (Cedars Sinai Medical Center, Los Angeles, Calif., USA), and MC-38, EL4, B16F10, Renca, CT26 and YAC-1 were purchased from American Type Culture Collection (ATCC, Manassas, Va., USA).

The results are shown as the mean±standard deviation (SD). Statistical analysis was performed using a Student's t-test. A P value <0.05 was considered to reflect a statistically significant difference.

Example 1

Manufacture of Dentritic Cell Vaccine Pulsed with mPlk1 RNA

Example 1-1

Cloning of Mouse Plk1 cDNA from CL26 tumor cell was used as a mouse PlK1 template for polymerase chain reaction (PCR) amplification. PCR reaction condition: 30 cycles of 2 min at 94° C., 15 sec at 94° C., 30 sec at 60° C. and 1 min at 72° C.; and 10 min at 72° C. Primers for mouse Plk1 are 5'-ccc aagctt (HindIII) ATG AAT GCA GCG GCC AAA GCT G-3'(Forward primer) and 5'-cg gaattc (EcoR I) CTA GGA GGC CTT GAG GCG GTT G-3'(reverse primer). PCR products were cloned into pcDNA3.1 vector (Invitrogen, Grand island, NY, USA). And the cloned gene was confirmed by base sequencing analysis.

Example 1-2

Culture of Bone Marrow-Derived Dentritic Cells

In order to obtain dendritic cells, bone marrow cells were taken from the shinbone marrow and a thighbone marrow of C57BL/6 mice. And, erythrocytes were removed by using buffer solution (hypotonic buffer, 9.84 g/L NH4Cl, 1 g/L KHCO3, and 0.1 mM EDTA). Dendritic cells were prepared from Balb/c mice for vaccination of CT26 tumor model. Said cells were washed 2 times with serum-free RPMI-1640 medium, and cultured at a concentration of $5 \times 10^6$ cells/well in complete RPMI-1640 comprising 10 ng/mL granulocyte-macrophage colony-stimulating factor (GM-CSF, e-bioscience, San Diego, Calif., USA) and 10 ng/mL recombinant murine interleukin-4 (IL-4, e-bioscience) derived from rodents. After 48 h, nonadherent cells were removed, supplemented with complete medium comprising CSF and IL-4. At the 6th day of culture, nonadherent and loose-adherent cells (Dendritic cells) were collected and used for RNA electroporation.

Example 1-3

Plk1 mRNA Electroporation into Dendritic Cells

Mouse Plk1/pcDNA3.1 plasmids were linearized by ScaI. The linearized DNA was used as a template for in vitro transcription by using the mMessage mMachine T7 Ultra Kit (Ambion, Austin, Tex. USA). At this time, mRNA concentration and quality were measured by spectrophotometry and agarose-gel electrophoresis. RNA samples were aliquoted and stored at −70° C. After 6 days of culture, dendritic cells were suspended in Opti-MEM medium to the concentration of $2.5 \times 10^7$ cells/mL, then the above suspension 200 μl was put in cuvette and RNA 20 μg was added. The cell suspension was put in electroporator (ElectroSquarePorator, ECM 830, BTX, San Diego, Calif., USA) and applied with 300V electric current for 500 μs. RNA transfered cells were immediately removed from the cuvette, then placed in complete medium containing GM-CSF, IL-4, and LPS (1 μg/mL: Sigma, Saint Louis, Mo., USA) to allow the DCs to fully mature for 24 h.

Transfer efficiency of electrophoresed dendritic cells was measured with EGFP RNA by FACS analysis.

Example 2

Manufacture of Dentritic Cell Vaccine Pulsed with huPlk1 RNA

Example 2-1

Cloning of Human Plk1 cDNA from HeLa tumor cell was used as a human PlK1 template for polymerase chain reaction (PCR) amplification. PCR reaction condition: 30 cycles of 2 min at 94° C., 15 sec at 94° C., 30 sec at 60° C. and 1 min at 72° C.; and 10 min at 72° C. Primers for human P1k1 are 5'-ATG AGT GCT GCA GTG ACT TCA GGG AA-3'(forward primer) and 5'-TTA GGA GGC CTT GAG ACG GTT GCT-3'(reverse primer). PCR products are cloned into pcDNA3.1 TOPO vector (Invitrogen, Grand island, NY, USA). And the cloned gene was confirmed by base sequencing.

Example 2-2

Culture of Human Dendritic Cells Derived from CD14+ Mononuclear Cells

In order to obtain human dendritic cells in vitro, immature dendritic cells from CD14+ mononuclear cells were cultured in RPMI 1640 medium with 10% fetal bovine serum, 100 ng/ml IL-4 (IL-4, Genzyme Cambridge, Mass., USA) at humidified 37° C. in 5% $CO_2$ incubator at 3 days intervals for 6 days.

Example 2-3

Plk1 mRNA Electroporation into Human Dendritic Cells

Human Plk1/pcDNA3.1 TOPT plasmid was linearized with ScaI. The linearized DNA was used as a template for in vitro transcription by using the mMessage mMachine T7 Ultra Kit (Ambion, Austin, Tex. USA). In vitro transcription process was performed using mMessage mMachine T7 Ultra machine kit (Ambion). Template is pcDNA3.1 Plk1 linerized DNA. T7 RNA polymerase, ribonucleotide mix, transcription mix, and template DNA are mixed and reacted for 2 h at 37° C. And then A tailing was performed with poly A polymerase for 30 minutes at 37° C. From the mixture completed with A tailing, template DNA was removed by Dnase. And each tumor antigen RNA of P1k1 RNA was collected by phenol/chloroform extraction method and ethanol precipitation method. Concentration of the collected RNA was measured by nanodrop spectrophotometry (ND-1000, USA). The transfer method of tumor antigen RNA into human dendritic cells was as following. Human immature dendritic cells were washed twice with Opti-MEM medium, suspended in 200 ul mixed with tumor antigen RNA 40 ug per $1\times10^6$ dendritic cells, and transferred by electroporator (BTX, USA) at 300V electric current for 500 µs. Then the cells were matured in dendritic cell medium containing LPS 1 ug/ml and TNF-alpha 200 unit/ml for more than 18 h. Transfer efficiency of electrophoresed dendritic cells was measured with EGFP RNA by using FACS analysis.

Example 3

Plk1 Expression

Mouse tumor cell line, human tumor cell line and mouse normal tissue were cut into small pieces by scalpel. And the small pieces were suspended in cell lysis buffer containing cocktail inhibitor (promega, Madison, Wis.). The suspension was homogenized by using Precellys 24 lyser (Bertin Technologies, Cedex, France). And cancer cells were lysed by the same cell lysis buffer. Protein concentration was measured by bicinchoninic acid assay (Pierce, Rockford, Ill., USA). Total protein (50 µg) was separated on 8% polyacrylamide gel. Following boltting onto nitrocellulose membrane (Schleicher & Schuell, Dassel, Germany), the blotted membrane was incubated with anti-Plk1 antibody (Cell signaling technology, Danvers, Mass., USA). Bands on nitrocellulose membrane were visualized by ECL (enhanced chemiluminescence) satin method (Amersham Pharmacia, Freiburg, Germany).

Plk1 expression in mouse and human tumor cells lines and in normal mouse tissues was analyzed by Western blotting. As shown in FIG. 1a, Mouse tumor cells strongly expressed mouse Plk1 in B16F10 (H-2b: melanoma), EL4 (H-2b: thymoma), MC-38 (H-2b: colon cancer), GL26 (H-2b: gliomas), Renca (H-2d: renal cancer), and CT26 (H-2d: colon cancer), but it was weakly expressed in YAC-I (H-2a: lymphoma). As shown in FIG. 1b, Human Plk1 was also expressed in human tumor cell lines that originated from a range of different organs: SKOV3 (ovarian cancer), MCF7 (breast cancer), T98G (glioblastoma), LoVo (colon cancer), SK-MEL5 (melanoma), K562 (leukemia), and HeLa (cervical cancer). As shown in FIG. 1c, Plk1 was not detected in the brain, lymph node, bone-marrow, lung, liver, kidney, and small and large intestine of the normal C57BL/6 mice, but was weakly expressed in the spleen. These results confirm that Plk1 protein is strongly expressed in most of tumor cells.

Example 4

Isolation of CD4+ and CD8+ T Cells

To measure CD4+ and CD8+ T lymphocytes immune response, splenocytes were incubated with magnetic beads conjugated to CD4- or CD8-specific monoclonal antibodies (magnetic antibody cell sorter [MACS]) for 15 min at 4° C. After incubation, the cells were washed in PBS with 2 nM EDTA and passed through a MACS magnetic separation column. The purity of each T lymphocytes after sorting was >90%, as determined by FACS analysis. Further, in order to isolate human lymphocytes and monocyte cells by MACS system, after density gradient, CD14+, CD4+ T and CD8+ T lymphocytes were isolated by using anti-CD14, anti-CD4 and anti-CD8 conjugated to magnetic microbeads (Miltenyi Biotec, Germany) in accordance with manual of MACS System (Miltenyi Biotec, Germany). The purity of each, T cell population after sorting was >95%, as determined by flow cytometric analysis.

Example 5

Enzyme-Linked ImmunoSpot (ELISPOT) Assay

ELISPOT kit was purchased from BD Bioscience (Qume Drive, San Jose, Calif., USA) and performed as instructions of the manufacturer. Spleen lymphocytes ($5\times10^4$ cells/well) were seeded in 96 well plate coated with anti-mouse IFN-γ antibody. The plate was treated with mPlk1RNA/DCs, mSuvRNA/DCs, CEARNA/DCs and DCs as target cell. Following incubation of the plate for 20 h at 37° C., the cells were removed, and the plate was washed three times with PBS. Then, the cells was added with anti-mouse IFN-γ antibody conjugated with biotin, and incubated for 2 h at RT. After plate was washed 3 times, streptavidin-horseradish peroxidase was added in each well and incubated for 1 h at RT. After washing the plate, 3-amino-9-ethly-carbazole (AEC) was added in each well. After spot was presented, the reaction was quenched by distilled water. And the plate was dried in darkroom for 24 h. Number of spots corresponding to IFN-γ-producing T cells was measured by automatic AID-ELISPOT-reader (Strassberg, Germany).

Figure 2:
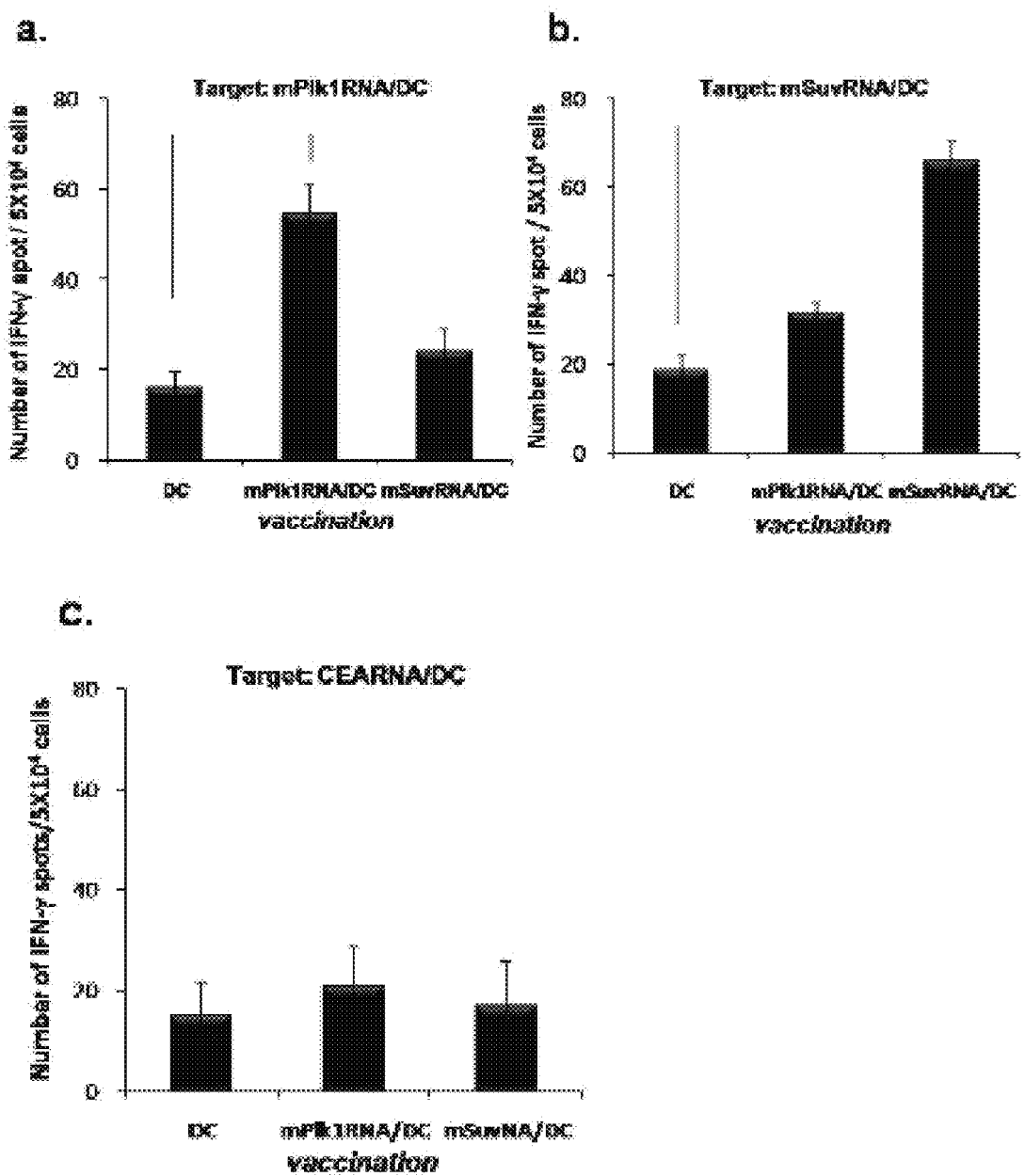
FIG. 2 shows levels of interferon (IFN)-γ-producing T cells following vaccination with mPlk1RNA/DCs and mSuvRNA/DCs.

As shown in FIG. 2a and FIG. 2b, we found that mPlk1RNA/DCs and mSuvRNA/DCs vaccination could induce Plk1- and Suv-specific IFN-γ-producing T cells, respectively in vitro. However, As shown in FIG. 2b and FIG. 2c, mPlk1-specific T cells did not significantly respond to mSuvRNA/DC and CEARNA/DC as irrelevant targets. These results indicate that Plk1-specific immune responses can be induced by mPlk1RNA/DC vaccination.

Figure 3:
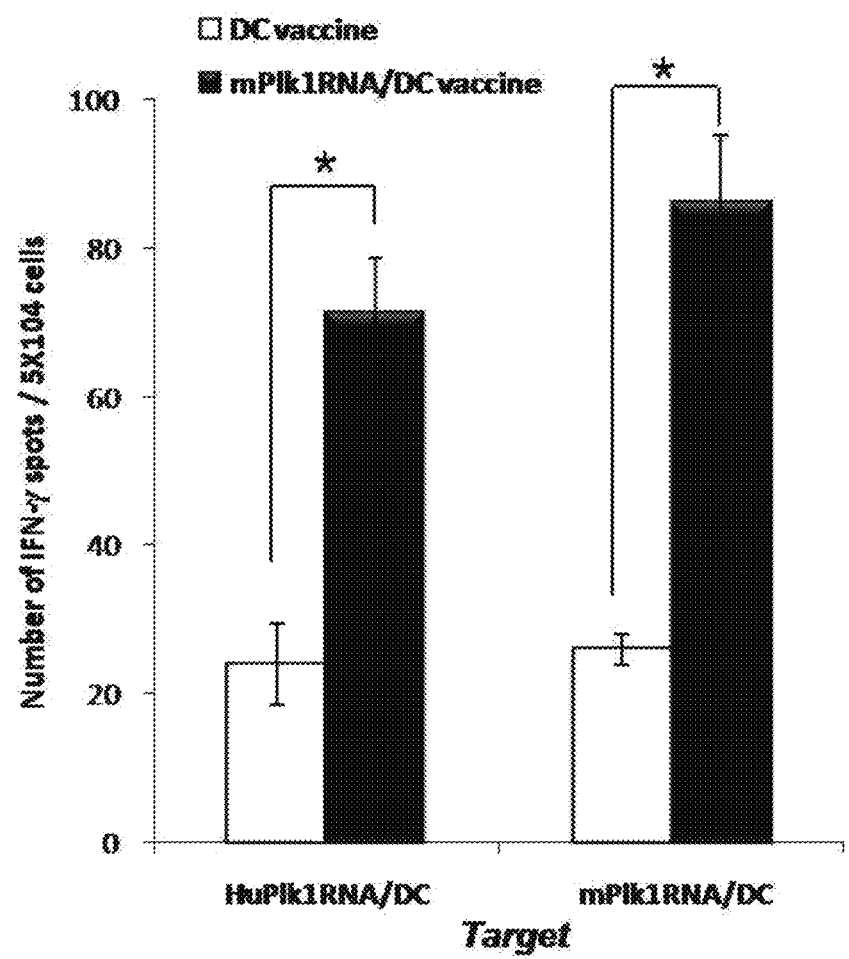
FIG. 3 shows levels of interferon (IFN)-γ-producing T cells following vaccination with mPlk1RNA/DCs and mSuvRNA/DCs.

In addition, to investigate the cross-reactivity between mouse and human Plk1, splenocytes from mice vaccinated with either mPlk1RNA/DCs or unpulsed DCs were stimulated with humanPlk1RNA/DC and mPlk1RNA/DC in vitro for an IFN-γ-ELISPOT assay. As shown in FIG. 3, mPlk1-specific T cells recognized humanPlk1 with levels similar to mPlk1. These data indicate that because of the high degree of amino acid homology between mouse and human Plk1, human Plk1RNA/DC can trigger effective Plk1-specific immune responses in mice, both in vitro and in vivo.

Example 6

Cytotoxicity Assay

Figure 4:
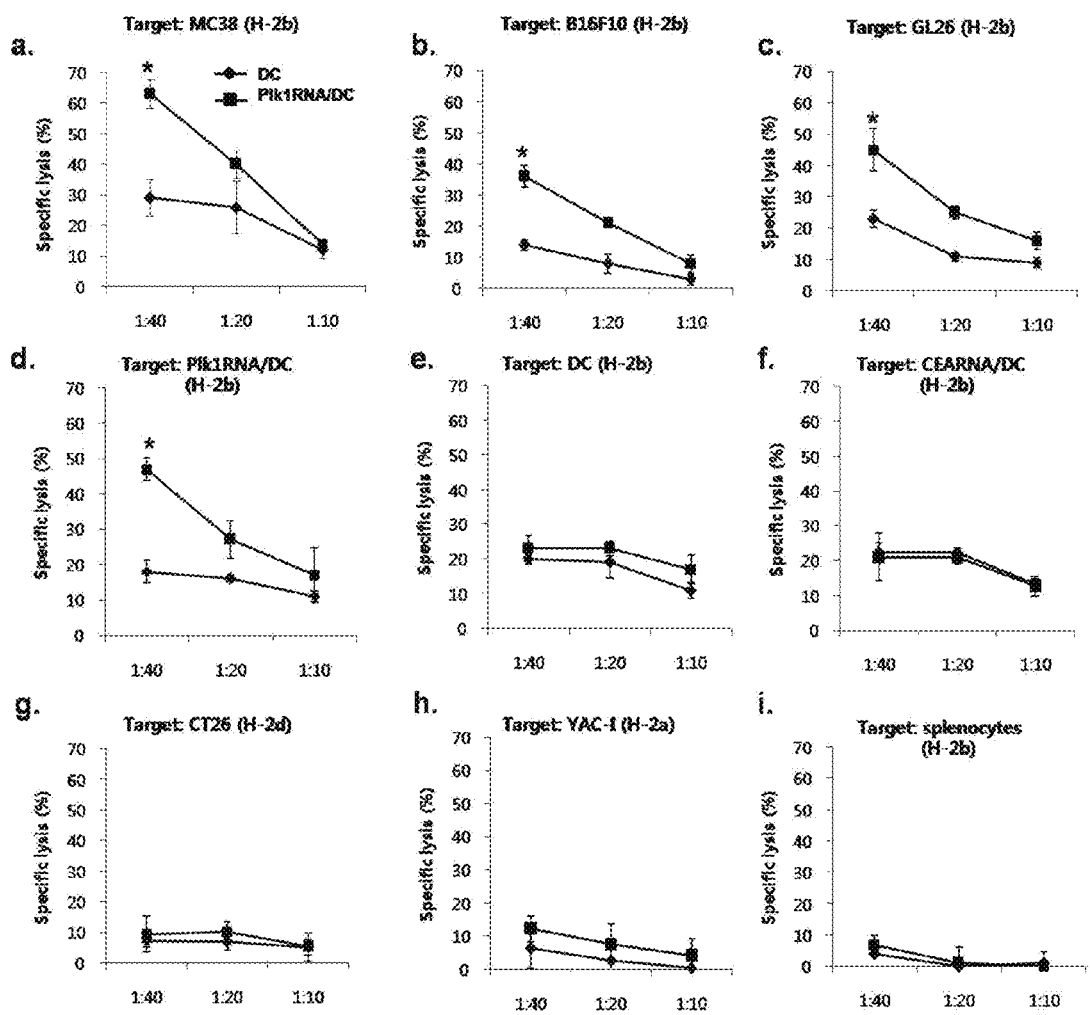
FIG. 4 shows cytotoxic activities following vaccination with mPlk1RNA/DCs.

Standard $^{51}$Cr-release assay was performed as follows. Splenocytes were extracted from each mouse. Splenocytes were reactivated in vitro by 4% paraformaldehyde-fixed MC-38 cell for 5 days, then the splenocytes were used as effector cells. MC-38, GL26, mPlk1RNA/DCs, CEARNA/DCs, DCs, YAC-1, CT26, and normal splenocytes were labeled with 100 mCi [$^{51}$C]-sodium chromate/1×10$^6$ cells for 1 h at 5% $CO_2$, 37° C., and used as target cells. $^{51}$Cr-labeled target cells were cultured with effector cells for 4 h at 37° C. Supernatant 100 μl of each well was collected and radioactivity was measured by gamma counter. Specific cell lysis rate=100×[(experiment release−spontaneous release)/(maximum release−spontaneous release)]. Wherein the spontaneous release and maximum release were respectively measured with medium and 2% triton X100. We evaluated the cytotoxic activity of splenocytes vaccinated with mPlk1RNA/DC in Plk1-expressing and Plk1-non-expressing targets. As shown in FIG. 4a to td, cytotoxic activity was shown only against H-2b haplotype matched (H-2b) Plk1-expressing targets (MC-38, B16F10, GL26, and mPlk1RNA/DCs). But as shown in FIGS. 4e to 4g, cytotoxic activity was not shown against Plk1-non-expressing targets (DCs and CEARNA/DCs) and H-2b haplotype mismatched target (H-2d). As shown in FIGS. 4h and 4i, YAC-1 and normal splenocytes targeted with NK cells did not show lysis reaction. These results indicate that mPlk1-specific immune responses can be induced by mPlk1RNA/DC vaccination.

Example 7

DC Vaccination and Tumor Models

For MC-38 tumor model, C57BL/6 mice (6-8 weeks old) were subcutaneously injected with 2×10$^5$ MC-38 cells. On day 2 after MC-38 cell inoculation, the mice were subcutaneously vaccinated with 1×10$^6$ mPlk1RNA/DCs, MC38TL/DCs, mSuvRNA/DCs, or DC once per a week for three weeks. For B16F10 tumor model, C57BL/6 mice (6-8 weeks old) were subcutaneously injected with 2×10$^5$ B16F10 cells. On day 1 after B16F10 cell inoculation, the mice were subcutaneously vaccinated with 1×10$^6$ mPlk1RNA/DCs, mSuvRNA/DCs, B16F10TL/DCs, or DC once per a week for three weeks. For CT26 tumor model, Balb/c mice (6-8 weeks old) were subcutaneously injected with 2×10$^5$ CT26 cells. On day 1 after CT26 cell inoculation, the mice were subcutaneously vaccinated with 1×10$^6$ cells mPlk1RNA/DCs, mSuvRNA/DCs, or DC once per a week for three weeks. To test the effects of xenogenic human Plk1, MC-38-tumor bearing mice were vaccinated three times with 1×10$^6$ humanPlk1RNA/DCs or DCs at 7 days intervals. Survivin is known tumor antigen used positive control. DCs transferred without RNA was used as a negative control. Decrease of tumor growth was compared with negative control.

Figure 5:
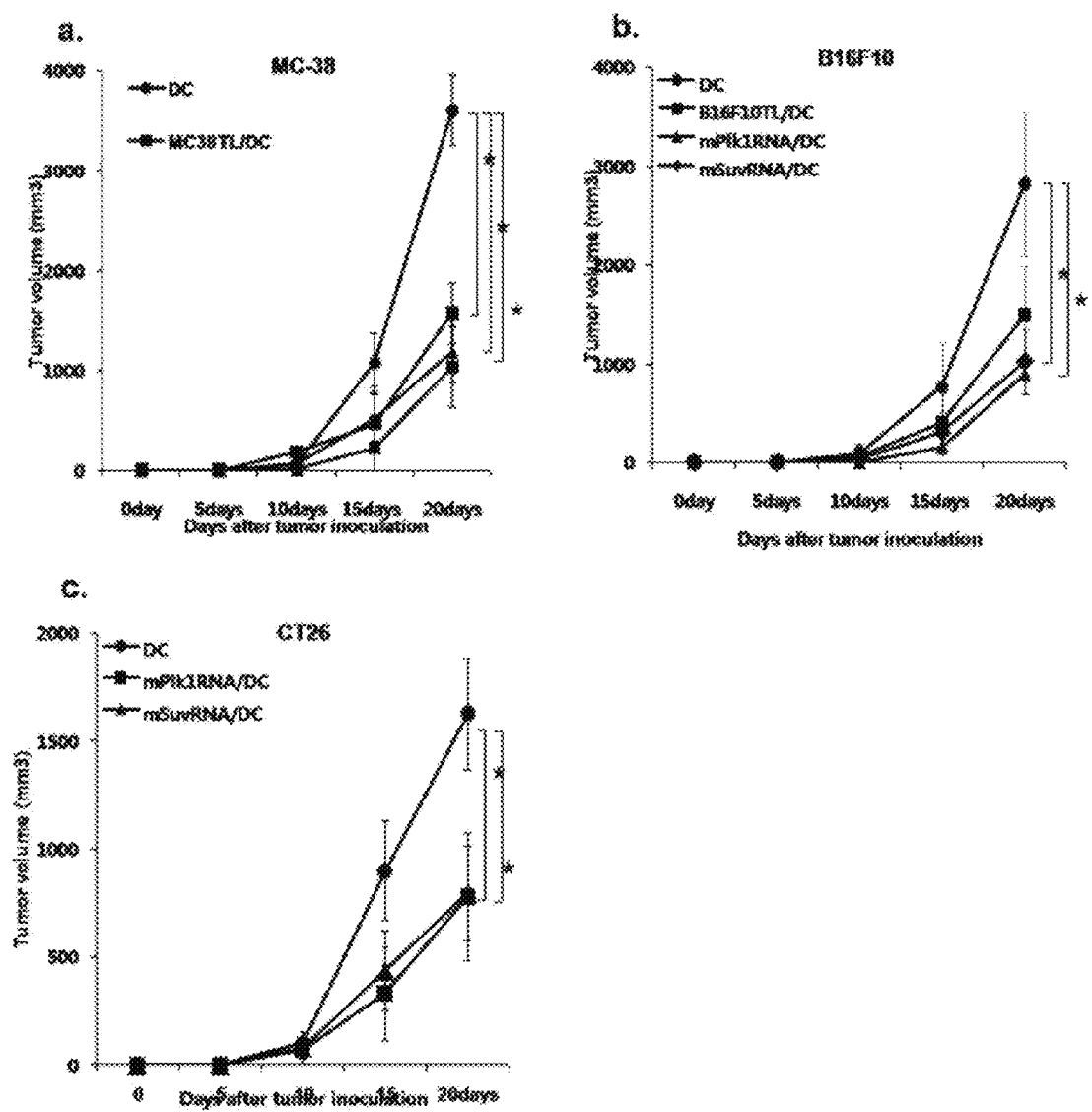
FIG. 5 shows tumor growth suppression following vaccination with mPlk1RNA/DCs and mSuvRNA/DCs.

To demonstrate the potential of Plk1 as a target tumor antigen for cancer immunotherapy, the antitumor effects of mPlk1RNA/DCs vaccination were observed and compared with that of mSuvRNA/DCs vaccination in various tumor models. As shown in FIGS. 5a to 5c, vaccination with mPlk1RNA/DCs provided a significant degree of therapeutic effects in MC-38 and B16F10 tumor models in C57BL/6 mice, 20 days after tumor inoculation. The mPlk1RNA/DCs vaccination also inhibited tumor growth in the C26 tumor model in BALB/c mice. The tumor inhibition induced by mPlk1RNA/DCs vaccination was similar to that of mSuvRNA/DCs vaccination. These results suggest that Plk1 may be used as tumor antigen, such as surviving which has been already recognized as a universal tumor antigen.

Figure 6:
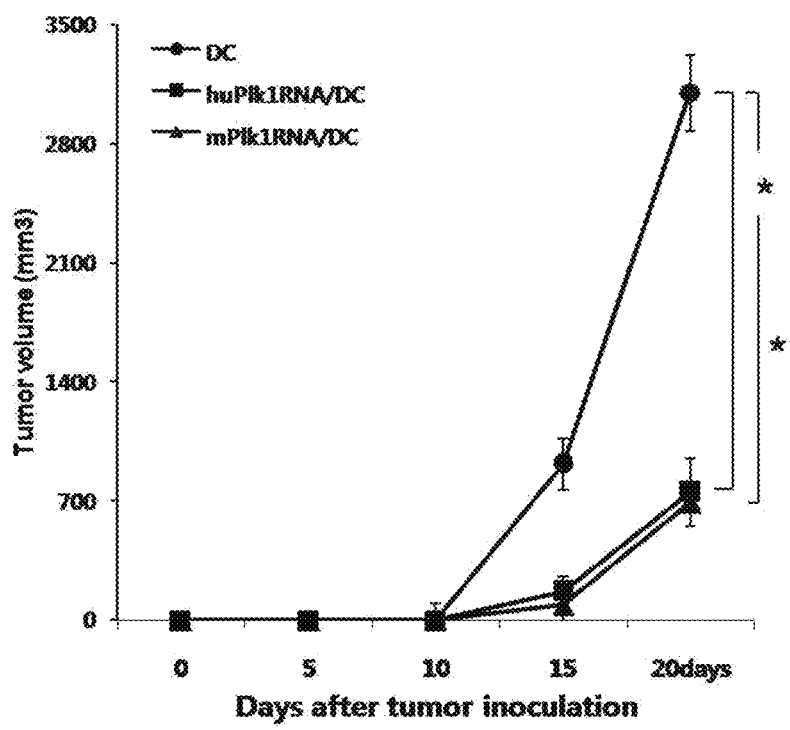
FIG. 6 shows tumor growth suppression following vaccination with mPlk1RNA/DCs and huPlk1RNA/DCs.

In addition, in order to evaluate anti-cancer effect by human Plk1, MC-38-bearing mice were vaccinated with human Plk1 RNAs pulsed DCs. As shown in FIG. 6, tumor growth was significantly decreased in mice vaccinated with huPlk1RNA/DCs similarly as mPlk1RNA/DCs. These results are caused by high homology of amino acid between mouse and human Plk1, and shows that human Plk1RNA/DC may induce effective Plk1-specific immune response in vivo.

Example 8

In Vivo Depletion of T Lymphocytes

To determine which subset of the T cells was involved in the antitumor effects induced by vaccination with mPlk1RNA/DC in MC-38 tumor model, CD4$^+$ or CD8$^+$ T cells were depleted by treatment with anti-CD4 (GK1.5; eBioscience) or with anti-CD8 monoclonal antibody (2.43: a gift from Prof. Byoung S. Kwon in Ulsan University, Ulsan, Korea), respectively. C57BL/6 mouse was intraperitoneally injected with purified anti-mouse CD4 or CD8 antibody or IgG 100 μg after 0, 7, 14 days of innoculation with 2×10$^5$ MC-38 cells. After 2 days of antibody injection, C57BL/6 mouse was subcutaneously injected with mPlk1RNA/DC. Removal of CD4$^+$ and CD8$^+$ (>95%) during the treatment was confirmed using FACS assay with CD4 and CD8 specific antibody. As control, dendritic cells without tumor antigen were vaccinated for normal tumor growth.

Figure 7:
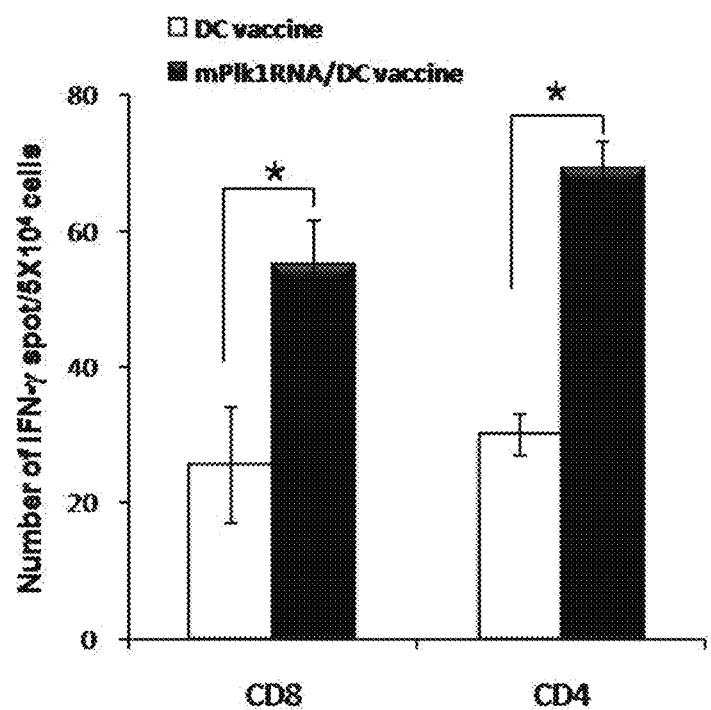
FIG. 7 shows levels of interferon (IFN)-γ-producing T cells of CD4+ and CD8+ T lymphocytes following vaccination with mPlk1RNA/DCs.

Plk1 expressing mRNA was used as an antigen, we examined the immune responses of CD4+ and CD8+ T cells. CD4+ and CD8+ T lymphocytes were sorted from splenocytes of mice vaccinated with either mPlk1RNA/DCs and unpulsed DCs, and were then stimulated with mPlk1RNA/DC. As shown in FIG. 7, both of CD4+ and CD8+ T lymphocytes represented high frequency of IFN-γ-producing T cells by vaccination with mPlk1RNA/DCs. These results indicate that Plk1-specific immune responses can be induced in vivo.

Figure 8:
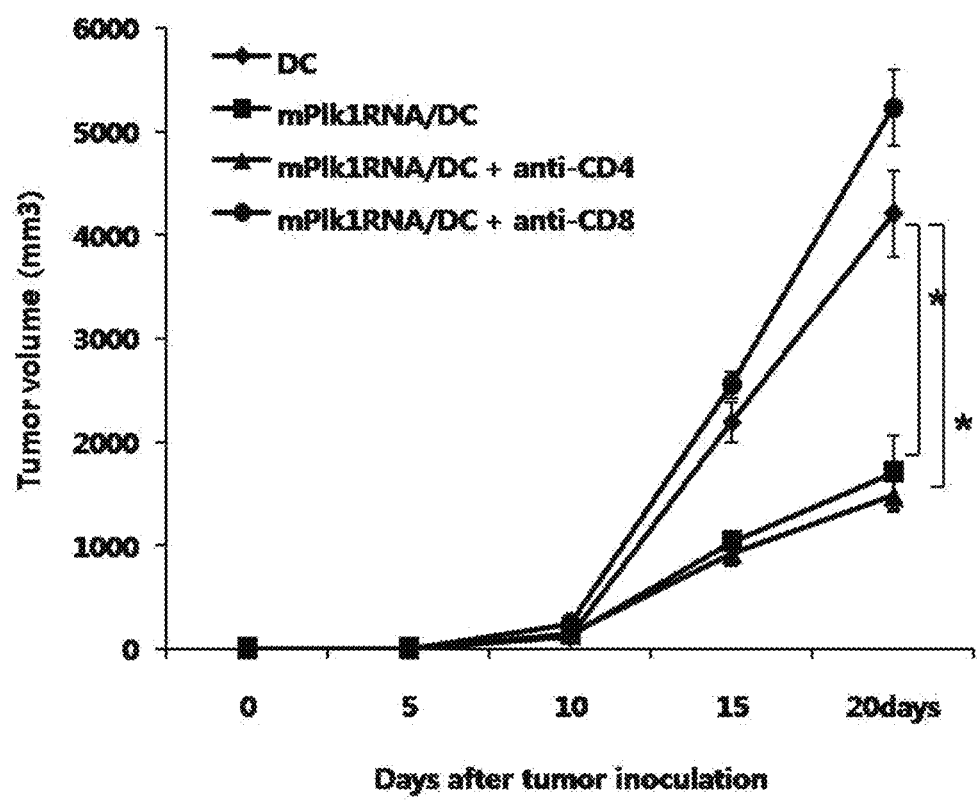
FIG. 8 shows tumor growth suppression of CD4+ and CD8+ T lymphocytes following vaccination with mPlk1RNA/DCs.

As shown in FIG. 8, depletion of CD8+ T lymphocytes significantly reversed the inhibition of tumor growth in mice vaccinated with mPlk1RNA/DCs, whereas depletion of CD4+ T cells did not. These data suggest that CD8+ T cells are the main effector cells involved in antitumor immunity in vivo.

Example 9

In Vitro Inducement of P1k1-Specific CTLs

In order to induce P1k1-specific cytotoxicity T cells (CTLs) in vitro, huP1k-1 RNA antigen pulsing was performed using the same method as Example 2-3. Then, mature dendritic cells were used as P1k1 antigen stimulating cells, and radio irradiated with 40 Gy to prevent the more growth of DCs. In addition, in order to obtain response cells which can be used to induce P1k-1-specific cytotoxicity T cells in vitro, a fraction of peripheral blood mononucleated cells which does not contain CD14 was used as materials to produce CD8+ and CD4+ T cells. As in Example 4, CD8+ cells and CD4+ cells were separated using MACS system. In order to obtain T helper 1 (Th1) cells in vitro, CD4+ T cells were stimulated with anti-CD3 antibody (OKT3, 2 ug/mL) and anti-CD28 antibody (2 ug/mL) conjugated to plate in polarization condition for 4 days. Th1 condition contains IL-12 (5 ng/mL) and anti-IL-4 mAb (5 ug/mL). After 4 days, Th1 CD4+ T cells were harvested, and for characterization of the cells, the cells were stained by anti-human CD4OL antibody and anti-human CXCR3 antibody labelled with fluorescent substance. Thereby, polarization of Th1 CD4+ T cell was confirmed. Purified CD8+: Th1 polarization CD4 rate was 2:1. The cells were cultured in 24-well plate in RPMI 1640 medium supplemented with 10% fetal bovine serum (Gibco-BRL), 2 mM I-glutamine, and 1% penicillin-streptomycin (Cambrex) each at $2.0 \times 10^6$/well and $1.0 \times 10^5$/well final concentration with P1k1 RNA transfer mature dendritic cells. On 7 days after culture, the cells were harvested and restimulated. P1k1 RNA transfer mature dendritic cells were placed in plate at $1.0 \times 10^5$ cells/well density, and the harvested T cells were added at $1.0 \times 10^5$ cells/well density in the above plate. From 8 days after culture, 20 U/mL IL-2 (Endogen) was added once per 3 days. After three times restimulation, P1k1-specific immune response was measured. For this, dendritic cells sensitized or unsensitized with huP1k1 RNA were used as target cells, and dendritic cells sensitized with CEA RNA were used as control antigen to confirm P1K-1-specific CTLs. The above cells are cultured with human T lymphocytes for 24 h and followed with IFN-γ-ELISPOT assay.

Figure 9:
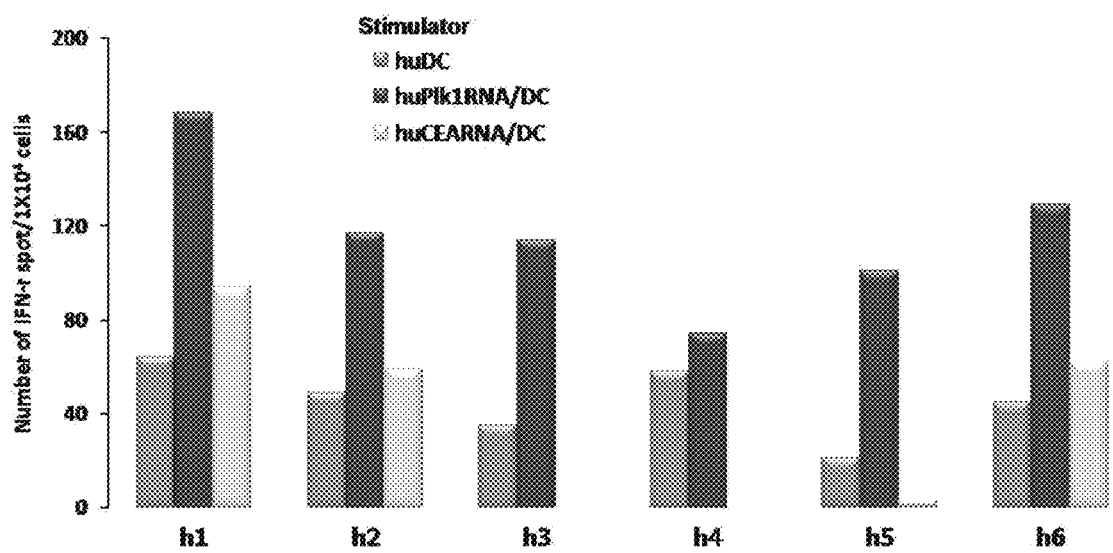
FIG. 9 shows levels of IFN-γ producing T cells stimulated with huPlk1RNA/DCs, huCEARNA/DCs and DCs to confirm in-vitro induced huPlk1-specific CTLs cellular immune response.

As a result, as shown in FIG. 9, in four healthy donors among six healthy donors (h1~h6), CEARNA/DN target cell group showed similar frequencies of IFN-γ to control DCs target cell group. IFN-γ-producing T cells showed the high frequencies in huP1k1RNS/DCs target cell group. These results, P1k-specific CILs are induced in vitro.

Figure 10:
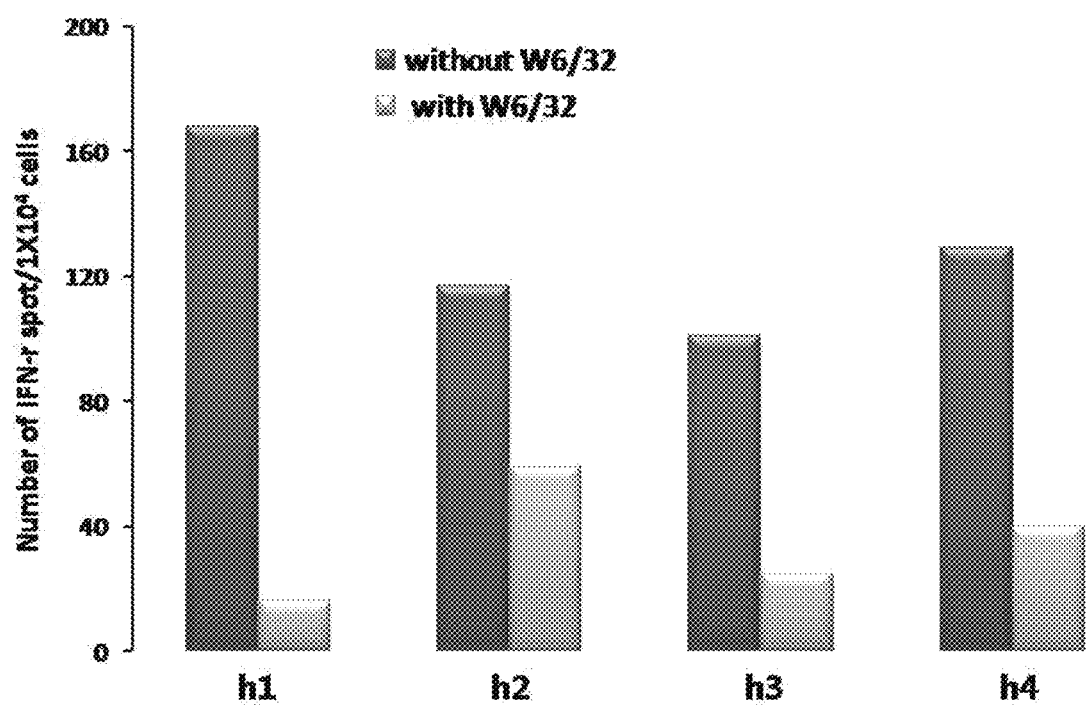
FIG. 10 shows levels of interferon (IFN)-γ-producing T cells of CD4+ and CD8+ T lymphocytes following CTL induction of huPlk1RNA/DCs.

In addition, the cells were pre-cultured with MHC class I blocking antibody (W6/32) for 30 min, and in order to confirm that P1k1 immune response is a response specific to CD8+ T lymphocytes, specific response of CD4+ T lymphocytes was observed by using MHC class I blocking antibody (W6/32). As shown in FIG. 10, in four healthy donors (h1~h4), CD8+ T lymphocytes showed 70-90% in three donors, 50% in one donor of IFN-γ-producing T cells frequencies by inducing a CTL response with huPlk1RNA/DNs. These results shows that effective P1k1-specific immune response was induced in vitro.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. An antigen-presenting cell which has a complex of MHC class I antigen or II antigen and a tumor antigen comprising a polo-like kinase 1-derived protein consisting of amino acid sequence of SEQ ID NO: 3, presented on the surface of cell having antigen-presentation capacity.

2. The antigen-presenting cell of claim 1, wherein the cell having antigen-presentation capacity is selected from the group consisting of dendritic cell, mononuclear cell, CD4 T cell, B cell and gamma delta T cell.

3. The antigen-presenting cell of claim 2, wherein CD4 T cell, B cell or gamma delta T cell is naive state, activated state or expanded state.

4. A composition for treating a tumor comprising, the antigen-presenting cell of claim 1.

5. A method for preventing or treating tumor, which comprises administering an effective dose of the antigen-presenting cell of claim 1.

6. The tumor antigen of claim 1, wherein the tumor antigen is encoded by a gene consisting of base sequence of SEQ ID NO: 4.

7. The composition of claim 4, wherein the tumor is selected from the group consisting of malignant melanoma, lymphoma, colorectal cancer, glioma, renal cancer, ovarian cancer, breast cancer, glioblastoma, leukemia and cervical cancer.

* * * * *

SEQUENCE LISTING

```
<160> NUMBER OF SEQ ID NOS: 4

<210> SEQ ID NO 1
<211> LENGTH: 603
<212> TYPE: PRT
<213> ORGANISM: Artificial Sequence
<220> FEATURE:
<223> OTHER INFORMATION: Mus musculus polo-like kinase 1

<400> SEQUENCE: 1

Met Asn Ala Ala Ala Lys Ala Gly Lys Leu Ala Arg Ala Pro Ala Asp
 1               5                   10                  15

Leu Gly Lys Gly Gly Val Pro Gly Asp Ala Val Pro Gly Ala Pro Val
            20                  25                  30

Ala Ala Pro Leu Ala Lys Glu Ile Pro Glu Val Leu Val Asp Pro Arg
        35                  40                  45

Ser Arg Arg Gln Tyr Val Arg Gly Arg Phe Leu Gly Lys Gly Gly Phe
    50                  55                  60
```

```
Ala Lys Cys Phe Glu Ile Ser Asp Ala Asp Thr Lys Glu Val Phe Ala
 65                  70                  75                  80

Gly Lys Ile Val Pro Lys Ser Leu Leu Leu Lys Pro His Gln Lys Glu
                 85                  90                  95

Lys Met Ser Met Glu Ile Ser Ile His Arg Ser Leu Ala His Gln His
            100                 105                 110

Val Val Gly Phe His Asp Phe Phe Glu Asp Ser Asp Phe Val Phe Val
        115                 120                 125

Val Leu Glu Leu Cys Arg Arg Arg Ser Leu Leu Glu Leu His Lys Arg
    130                 135                 140

Arg Lys Ala Leu Thr Glu Pro Glu Ala Arg Tyr Tyr Leu Arg Gln Ile
145                 150                 155                 160

Val Leu Gly Cys Gln Tyr Leu His Arg Asn Gln Val Ile His Arg Asp
                165                 170                 175

Leu Lys Leu Gly Asn Leu Phe Leu Asn Glu Asp Leu Glu Val Lys Ile
            180                 185                 190

Gly Asp Phe Gly Leu Ala Thr Lys Val Glu Tyr Glu Gly Glu Arg Lys
        195                 200                 205

Lys Thr Leu Cys Gly Thr Pro Asn Tyr Ile Ala Pro Glu Val Leu Ser
    210                 215                 220

Lys Lys Gly His Ser Phe Glu Val Asp Val Trp Ser Ile Gly Cys Ile
225                 230                 235                 240

Met Tyr Thr Leu Leu Val Gly Lys Pro Pro Phe Glu Thr Ser Cys Leu
                245                 250                 255

Lys Glu Thr Tyr Leu Arg Ile Lys Lys Asn Glu Tyr Ser Ile Pro Lys
            260                 265                 270

His Ile Asn Pro Val Ala Ala Ser Leu Ile Gln Lys Met Leu Gln Thr
        275                 280                 285

Asp Pro Thr Ala Arg Pro Thr Ile His Glu Leu Leu Asn Asp Glu Phe
    290                 295                 300

Phe Thr Ser Gly Tyr Ile Pro Ala Arg Leu Pro Ile Thr Cys Leu Thr
305                 310                 315                 320

Ile Pro Pro Arg Phe Ser Ile Ala Pro Ser Ser Leu Asp Pro Ser Ser
                325                 330                 335

Arg Lys Pro Leu Lys Val Leu Asn Lys Gly Val Glu Asn Pro Leu Pro
            340                 345                 350

Asp Arg Pro Arg Glu Lys Glu Glu Pro Val Val Arg Glu Thr Asn Glu
        355                 360                 365

Ala Ile Glu Cys His Leu Ser Asp Leu Leu Gln Gln Leu Thr Ser Val
    370                 375                 380

Asn Ala Ser Lys Pro Ser Glu Arg Gly Leu Val Arg Gln Glu Glu Ala
385                 390                 395                 400

Glu Asp Pro Ala Cys Ile Pro Ile Phe Trp Val Ser Lys Trp Val Asp
                405                 410                 415

Tyr Ser Asp Lys Tyr Gly Leu Gly Tyr Gln Leu Cys Asp Asn Ser Val
            420                 425                 430

Gly Val Leu Phe Asn Asp Ser Thr Arg Leu Ile Leu Tyr Asn Asp Gly
        435                 440                 445

Asp Ser Leu Gln Tyr Ile Glu Arg Asp Gly Thr Glu Ser Tyr Leu Thr
    450                 455                 460

Val Ser Ser His Pro Asn Ser Leu Met Lys Lys Ile Thr Leu Leu Asn
465                 470                 475                 480

Tyr Phe Arg Asn Tyr Met Ser Glu His Leu Leu Lys Ala Gly Ala Asn
```

|   |   | 485 |   |   |   | 490 |   |   |   | 495 |   |
|---|---|---|---|---|---|---|---|---|---|---|---|
| Ile | Thr | Pro | Arg | Glu | Gly | Asp | Glu | Leu | Ala | Arg | Leu |
|   |   | 500 |   |   |   | 505 |   |   |   | 510 |   |
| Pro | Tyr | Leu | Arg | Thr | Trp | Phe | Arg | Thr | Arg | Ser | Ala |
|   |   | 515 |   |   |   | 520 |   |   |   | 525 |   |
| Ile | Ile | Leu | His | Leu | Ser | Asn | Gly | Thr | Val | Gln | Ile |
|   |   | 530 |   |   |   | 535 |   |   |   | 540 |   |
| Asn | Phe | Phe | Gln | Asp | His | Thr | Lys | Leu | Ile | Leu | Cys |
| Pro | Leu | Met | Ala | Ala | Val | Thr | Tyr | Ile | Asn | Glu | Lys |
| 545 |   |   |   | 550 |   |   |   | 555 |   |   |   |
| Arg | Asp | Phe | Gln | Thr | Tyr | Arg | Leu | Ser | Leu | Leu | Glu |
|   |   |   | 560 |   |   |   |   | 565 |   |   |   |
| Glu | Tyr | Gly | Cys | Cys | Lys | Glu | Leu | Ala | Ser | Arg | Leu |
|   |   | 570 |   |   |   | 575 |   |   |   | 580 |   |
| Arg | Tyr | Ala | Arg | Thr | Met | Val | Asp | Lys | Leu | Leu | Ser |
|   |   |   | 585 |   |   |   |   | 590 |   |   |   |
| Ser | Arg | Ser | Ala | Ser | Asn | Arg | Leu | Lys | Ala | Ser |   |
|   |   | 595 |   |   |   | 600 |   |   |   |   |   |

<210> SEQ ID NO 2
<211> LENGTH: 1812
<212> TYPE: DNA
<213> ORGANISM: Artificial Sequence
<220> FEATURE:
<223> OTHER INFORMATION: Mus musculus polo-like kinase 1

<400> SEQUENCE: 2

```
atgaatgcag cggccaaagc tggaaagctg gctcgagcac cagccgacct cgggaaaggt      60
ggggttccgg gagatgcagt tcccggtgcc ccagtggccg cccgctggc gaaagaaatt      120
ccggaggtcc tagtggaccc acgcagccgg cggcagtatg tacggggcg ctttctgggt      180
aaaggaggct cgccaaatg cttcgagatc tcagacgcag acacaaaaga ggtgttcgca      240
ggcaagatcg tgcctaagtc tttgctgctc aagccccacc agaaggagaa gatgtctatg      300
gagatctcaa ttcaccgcag cctagcacac caacacgtcg taggcttcca tgacttttt      360
gaggacagcg actttgtatt tgtagttttg gagctctgtc gcaggaggtc cctcctggag      420
ctgcacaaga ggaggaaggc actgaccgag cctgaggccc gctactacct gcgacagata      480
gtcctgggct gccagtacct gcaccgcaat caggtcattc acaggaccct caagctgggc      540
aacctcttcc tgaacgagga tctggaggtg aaaatagggg attttggctt ggcaaccaaa      600
gtggaatatg aaggggaacg aaagaagacc ttgtgtggca ctcctaacta catagctcct      660
gaggtgctga gcaagaaggg acacagtttt gaggtggatg tgtggccat gggtgcatc      720
atgtatacct tgctagtggg caagcctccc tttgagacct cgtgcctaaa agagacctac      780
ctccggatca agaaaatga atacagtatt cccaagcaca tcaacccagt ggccgcctcc      840
ctcatccaga gatgcttca gacagacccc actgcccgcc ccaccattca cgagttgctc      900
aatgacgagt tcttcacttc tggctacatc cccgcccgtc ccctattac ctgcctcacc      960
atcccaccaa ggtttcaat cgctcccagc agcctggacc ccagcagcag gaaacctctc      1020
aaagtcctca ataaaggtgt ggagaacccc ctgcctgacc gtccccggga gaagaggaa      1080
ccggtggtcc gggagacaaa tgaggccatt gagtgccacc ttagtgactt gctacagcag      1140
ctgaccagtg tcaacgcctc caagcccctcg gagcgcgggc tggtgcggca agaggaggct      1200
gaggatcctg cctgcatccc catcttctgg gtcagcaagt gggtggacta ttcggacaag      1260
tatgccttg ggtatcagct gtgtgacaac agtgtggggg tgcttttta tgactcaaca      1320
cgcctgatt ctctacaatga cggggacagc ctgcagtaca tagagcgtga tggcacggag      1380
```

-continued

```
tcctatctca ctgtgagctc ccatcccaat tccttgatga agaagatcac tctcctcaac   1440
tatttccgca attacatgag tgagcacctg ctgaaggcag gggccaacat cacacccgg    1500 gaaggcgacg agctggcccg ctgccctac ctacgaacgt ggttccgcac acgcagcgcc    1560
atcatcctgc acctcagcaa cggcaccgtg cagattaact tcttccagga ccacaccaaa   1620
cttatcctgt gcccctgat ggcagcggtg acctacatca acgagaagag ggacttccaa    1680
acgtaccgcc tgagcctcct ggaggagtat ggctgctgca aggagctggc cagccgcctc   1740
cgctacgccc gcaccatggt agacaagctg ctgagctcgc gctccgccag caaccgcctc   1800
aaggcctcct ag                                                       1812
```

<210> SEQ ID NO 3
<211> LENGTH: 603
<212> TYPE: PRT
<213> ORGANISM: Artificial Sequence
<220> FEATURE:
<223> OTHER INFORMATION: Homo sapiens polo-like kinase 1

<400> SEQUENCE: 3

```
Met Ser Ala Ala Val Thr Ala Gly Lys Leu Ala Arg Ala Pro Ala Asp
 1               5                  10                  15

Pro Gly Lys Ala Gly Val Pro Gly Val Ala Ala Pro Gly Ala Pro Ala
                20                  25                  30

Ala Ala Pro Pro Ala Lys Glu Ile Pro Glu Val Leu Val Asp Pro Arg
            35                  40                  45

Ser Arg Arg Arg Tyr Val Arg Gly Arg Phe Leu Gly Lys Gly Gly Phe
        50                  55                  60

Ala Lys Cys Phe Glu Ile Ser Asp Ala Asp Thr Lys Glu Val Phe Ala
65                  70                  75                  80

Gly Lys Ile Val Pro Lys Ser Leu Leu Leu Lys Pro His Gln Arg Glu
                85                  90                  95

Lys Met Ser Met Glu Ile Ser Ile His Arg Ser Leu Ala His Gln His
               100                 105                 110

Val Val Gly Phe His Gly Phe Phe Glu Asp Asn Asp Phe Val Phe Val
            115                 120                 125

Val Leu Glu Leu Cys Arg Arg Arg Ser Leu Leu Glu Leu His Lys Arg
        130                 135                 140

Arg Lys Ala Leu Thr Glu Pro Glu Ala Arg Tyr Tyr Leu Arg Gln Ile
145                 150                 155                 160

Val Leu Gly Cys Gln Tyr Leu His Arg Asn Arg Val Ile His Arg Asp
                165                 170                 175

Leu Lys Leu Gly Asn Leu Phe Leu Asn Glu Asp Leu Glu Val Lys Ile
            180                 185                 190

Gly Asp Phe Gly Leu Ala Thr Lys Val Glu Tyr Asp Gly Glu Arg Lys
        195                 200                 205

Lys Thr Leu Cys Gly Thr Pro Asn Tyr Ile Ala Pro Glu Val Leu Ser
    210                 215                 220

Lys Lys Gly His Ser Phe Glu Val Asp Val Trp Ser Ile Gly Cys Ile
225                 230                 235                 240

Met Tyr Thr Leu Leu Val Gly Lys Pro Pro Phe Glu Thr Ser Cys Leu
                245                 250                 255

Lys Glu Thr Tyr Leu Arg Ile Lys Lys Asn Glu Tyr Ser Ile Pro Lys
            260                 265                 270

His Ile Asn Pro Val Ala Ala Ser Leu Ile Gln Lys Met Leu Gln Thr
        275                 280                 285
```

```
Asp Pro Thr Ala Arg Pro Thr Ile Asn Glu Leu Leu Asn Asp Glu Phe
    290                 295                 300
Phe Thr Ser Gly Tyr Ile Pro Ala Arg Leu Pro Ile Thr Cys Leu Thr
305                 310                 315                 320
Ile Pro Pro Arg Phe Ser Ile Ala Pro Ser Ser Leu Asp Pro Ser Asn
            325                 330                 335
Arg Lys Pro Leu Thr Val Leu Asn Lys Gly Leu Glu Asn Pro Leu Pro
            340                 345                 350
Glu Arg Pro Arg Glu Lys Glu Glu Pro Val Val Arg Glu Thr Gly Glu
        355                 360                 365
Val Val Asp Cys His Leu Ser Asp Met Leu Gln Gln Leu His Ser Val
    370                 375                 380
Asn Ala Ser Lys Pro Ser Glu Arg Gly Leu Val Arg Gln Glu Glu Ala
385                 390                 395                 400
Glu Asp Pro Ala Cys Ile Pro Ile Phe Trp Val Ser Lys Trp Val Asp
            405                 410                 415
Tyr Ser Asp Lys Tyr Gly Leu Gly Tyr Gln Leu Cys Asp Asn Ser Val
            420                 425                 430
Gly Val Leu Phe Asn Asp Ser Thr Arg Leu Ile Leu Tyr Asn Asp Gly
        435                 440                 445
Asp Ser Leu Gln Tyr Ile Glu Arg Asp Gly Thr Glu Ser Tyr Leu Thr
    450                 455                 460
Val Ser Ser His Pro Asn Ser Leu Met Lys Lys Ile Thr Leu Leu Lys
465                 470                 475                 480
Tyr Phe Arg Asn Tyr Met Ser Glu His Leu Leu Lys Ala Gly Ala Asn
            485                 490                 495
Ile Thr Pro Arg Glu Gly Asp Glu Leu Ala Arg Leu Pro Tyr Leu Arg
            500                 505                 510
Thr Trp Phe Arg Thr Arg Ser Ala Ile Ile Leu His Leu Ser Asn Gly
        515                 520                 525
Ser Val Gln Ile Asn Phe Phe Gln Asp His Thr Lys Leu Ile Leu Cys
    530                 535                 540
Pro Leu Met Ala Ala Val Thr Tyr Ile Asp Glu Lys Arg Asp Phe Arg
545                 550                 555                 560
Thr Tyr Arg Leu Ser Leu Leu Glu Glu Tyr Gly Cys Cys Lys Glu Leu
            565                 570                 575
Ala Ser Arg Leu Arg Tyr Ala Arg Thr Met Val Asp Lys Leu Leu Ser
            580                 585                 590
Ser Arg Ser Ala Ser Asn Arg Leu Lys Ala Ser
        595                 600

<210> SEQ ID NO 4
<211> LENGTH: 1812
<212> TYPE: DNA
<213> ORGANISM: Artificial Sequence
<220> FEATURE:
<223> OTHER INFORMATION: Homo sapiens polo-like kinase 1

<400> SEQUENCE: 4
atgagtgctg cagtgactgc agggaagctg gcacgggcac cggccgaccc tgggaaagcc     60
ggggtccccg gagttgcagc tcccggagct ccggcggcgg ctccaccggc gaaagagatc    120
ccggaggtcc tagtggaccc acgcagccgg cggcgctatg tgcggggccg ctttttgggc    180
aagggcggct tgccaagtg cttcgagatc tcggacgcgg acaccaagga ggtgttcgcg    240
```

```
ggcaagattg tgcctaagtc tctgctgctc aagccgcacc agagggagaa gatgtccatg    300
gaaatatcca ttcaccgcag cctcgcccac cagcacgtcg taggattcca cggcttttc    360 gaggacaacg acttcgtgtt cgtggtgttg gagctctgcc gccggaggtc tctcctggag    420
ctgcacaaga ggaggaaagc cctgactgag cctgaggccc gatactacct acggcaaatt    480
gtgcttggct gccagtacct gcaccgaaac cgagttattc atcgagacct caagctgggc    540
aaccttttcc tgaatgaaga tctggaggtg aaaatagggg attttggact ggcaaccaaa    600
gtcgaatatg acggggagag gaagaagacc ctgtgtggga ctcctaatta catagctccc    660
gaggtgctga gcaagaaagg gcacagtttc gaggtggatg tgtggtccat tgggtgtatc    720
atgtatacct tgttagtggg caaaccacct tttgagactt cttgcctaaa agagacctac    780
ctccggatca agaagaatga atacagtatt cccaagcaca tcaacccgt ggccgcctcc    840 ctcatccaga agatgcttca gacagatccc actgcccgcc caaccattaa cgagctgctt    900
aatgacgagt tctttacttc tggctatatc cctgcccgtc tccccatcac ctgcctgacc    960
attccaccaa ggttttcgat tgctcccagc agcctggacc ccagcaaccg gaagcccctc    1020
acagtcctca ataaaggctt ggagaacccc ctgcctgagc gtccccggga aaagaagaa    1080 ccagtggttc gagagacagg tgaggtggtc gactgccacc tcagtgacat gctgcagcag    1140
ctgcacagtg tcaatgcctc caagccctcg gagcgtgggc tggtcaggca agaggaggct    1200
gaggatcctg cctgcatccc catcttctgg gtcagcaagt gggtggacta ttcggacaag    1260
tacggccttg ggtatcagct ctgtgataac agcgtggggg tgctcttcaa tgactcaaca    1320
cgcctcatcc tctacaatga tggtgacagc ctgcagtaca tagagcgtga cggcactgag    1380
tcctacctca ccgtgagttc ccatcccaac tccttgatga agaagatcac cctccttaaa    1440
tatttccgca attacatgag cgagcacttg ctgaaggcag gtgccaacat cacgccgcgc    1500
gaaggtgatg agctcgcccg gctgccctac ctacggacct ggttccgcac ccgcagcgcc    1560
atcatcctgc acctcagcaa cggcagcgtg cagatcaact tcttccagga tcacaccaag    1620
ctcatcttgt gcccactgat ggcagccgtg acctacatcg acgagaagcg ggacttccgc    1680
acataccgcc tgagtctcct ggaggagtac ggctgctgca aggagctggc cagccggctc    1740
cgctacgccc gcactatggt ggacaagctg ctgagctcac gctcggccag caaccgtctc    1800
aaggcctcct aa                                                        1812
```